(12) United States Patent
Rao et al.

(10) Patent No.: US 9,644,188 B2
(45) Date of Patent: May 9, 2017

(54) METHODS AND MOLECULES FOR SUPPRESSION OF RNA SILENCING

(71) Applicants: Aln Rao, Riverside, CA (US);
Jang-Kyung Seo, Riverside, CA (US)

(72) Inventors: Aln Rao, Riverside, CA (US);
Jang-Kyung Seo, Riverside, CA (US)

( * ) Notice: Subject to any disclaimer, the term of this patent is extended or adjusted under 35 U.S.C. 154(b) by 0 days.

(21) Appl. No.: 14/254,886

(22) Filed: Apr. 16, 2014

(65) Prior Publication Data

US 2016/0040133 A1 Feb. 11, 2016
US 2016/0251630 A9 Sep. 1, 2016

Related U.S. Application Data

(60) Provisional application No. 61/812,941, filed on Apr. 17, 2013.

(51) Int. Cl.
*C12N 7/00* (2006.01)
*C12N 7/02* (2006.01)
*A61K 39/12* (2006.01)
*C07K 14/005* (2006.01)

(52) U.S. Cl.
CPC .............. *C12N 7/00* (2013.01); *C07K 14/005* (2013.01); *C12N 7/025* (2013.01); *C12N 2770/30022* (2013.01); *C12N 2770/30043* (2013.01); *C12N 2770/30052* (2013.01)

(58) Field of Classification Search
CPC A61K 39/12; A61K 2039/525; C12N 15/113; C12N 2310/14; C12N 7/00; C12N 2770/30011; C12N 2770/30022; C12N 2770/00011; C12N 2770/00022
See application file for complete search history.

(56) References Cited

U.S. PATENT DOCUMENTS

| 2003/0157130 A1* | 8/2003 | Bensi | C07K 14/005 424/208.1 |
| 2003/0219407 A1* | 11/2003 | Ding | C07K 14/005 424/93.2 |
| 2006/0094055 A1 | 5/2006 | Ding et al. | |
| 2015/0267203 A1* | 9/2015 | Ding | C07K 14/005 514/44 A |

OTHER PUBLICATIONS

Dasgupta R. protein B2 [Flock house virus]. NCBI Reference Sequence: NP_689446.1. Dep Dec. 8, 2008.*
Seo et al. Molecular dissection of Flock house virus protein B2 reveals that electrostatic interactions between N-terminal domains of B2 monomers are critical for dimerization. Virology 432(2012) 296-305.
Vaucheret et al. Post-transcriptional gene silencing in plants. Journal of Cell Science 114(2001) 3083-3091.

* cited by examiner

*Primary Examiner* — Rachel B Gill

(57) ABSTRACT

Certain embodiments of the invention relate to mutant forms of flock house virus B2 protein characterized by having enhanced suppressor of RNA silencing activity as compared to wild type flock house virus B2 protein. Certain embodiments of the invention relate to nucleic acid sequences and vectors that encode and/or direct expression of such mutant forms of flock house virus B2 protein in eukaryotic cells. Certain embodiments of the invention relate to methods of using such mutant forms of flock house virus B2 protein and/or nucleic acid sequences and vectors that encode and/or direct expression thereof in eukaryotic cells to increase a replication rate of a plant or animal virus in a plant or animal cell.

16 Claims, 13 Drawing Sheets

```
                    SEQ ID NO: 10              SEQ ID NO: 11
                    MPSKLALIQELPDRIQ           LEERLRKLELSHSLPTTGSDPPPAKL
                    ┌──────────────┐           ┌────────────────────────┐
                    1     17                   81                    106
           ┌────────────────────────────────────────────────────────────┐
    B2 wt  │                                                            │
           └────────────────────────────────────────────────────────────┘

18                                          106
                          ┌──────────────────────────────────────────┐
    B2 Δ1-17    -----     │                                          │
                          └──────────────────────────────────────────┘

1                                                89
           ┌──────────────────────────────────────────────────┐
    B2 Δ90-106 │                                              │     -----
           └──────────────────────────────────────────────────┘

SEQ ID NO: 12
                    MPSALALIQALPAAIQ
                    ┌──────────────┐
                    1     17                                          106
           ┌────────────────────────────────────────────────────────────┐
    B2 N-4ASM │                                                         │
           └────────────────────────────────────────────────────────────┘

SEQ ID NO: 13
                                        LAAALAALALSASLPTTGSAPPPAAL
                                        ┌────────────────────────┐
                                        81                    106
           ┌────────────────────────────────────────────────────────────┐
    B2 C-9ASM │                                                         │
           └────────────────────────────────────────────────────────────┘
```

Figure 4A

| | | 105 |
|---|---|---|
| | 1 | 30 |

B2 wt    MPSKLALIQELPDRIQTAVEAAMGMSYQDA    SEQ ID NO: 14

B2 K4A   MPSALALIQELPDRIQTAVEAAMGMSYQDA    SEQ ID NO: 15

B2 E10A  MPSKLALIQALPDRIQTAVEAAMGMSYQDA    SEQ ID NO: 16

B2 D13A  MPSKLALIQELPARIQTAVEAAMGMSYQDA    SEQ ID NO: 17

B2 R14A  MPSKLALIQELPDAIQTAVEAAMGMSYQDA    SEQ ID NO: 18

B2 E20A  MPSKLALIQELPDRIQTAVAAAMGMSYQDA    SEQ ID NO: 19

B2 D29A  MPSKLALIQELPDRIQTAVEAAMGMSYQAA    SEQ ID NO: 20

Figure 4B

SEQUENCE LISTING

<160> NUMBER OF SEQ ID NOS: 20

<210> SEQ ID NO 1
<211> LENGTH: 106
<212> TYPE: PRT
<213> ORGANISM: flock house virus

<400> SEQUENCE: 1

Met Pro Ser Lys Leu Ala Leu Ile Gln Glu Leu Pro Asp Arg Ile Gln
1               5                   10                  15

Thr Ala Val Glu Ala Ala Met Gly Met Ser Tyr Gln Asp Ala Pro Asn
            20                  25                  30

Asn Val Arg Arg Asp Leu Asp Asn Leu His Ala Cys Leu Asn Lys Ala
        35                  40                  45

Lys Leu Thr Val Ser Arg Met Val Thr Ser Leu Leu Glu Lys Pro Ser
    50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Pro Ala Lys Leu
            100                 105

<210> SEQ ID NO 2
<211> LENGTH: 106
<212> TYPE: PRT
<213> ORGANISM: Artificial sequence
<220> FEATURE:
<223> OTHER INFORMATION: B2 N-4ASM

<400> SEQUENCE: 2

Met Pro Ser Ala Leu Ala Leu Ile Gln Ala Leu Pro Ala Ala Ile Gln
1               5                   10                  15

Thr Ala Val Glu Ala Ala Met Gly Met Ser Tyr Gln Asp Ala Pro Asn
            20                  25                  30

Asn Val Arg Arg Asp Leu Asp Asn Leu His Ala Cys Leu Asn Lys Ala
        35                  40                  45

Lys Leu Thr Val Ser Arg Met Val Thr Ser Leu Leu Glu Lys Pro Ser
    50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Pro Ala Lys Leu
            100                 105

<210> SEQ ID NO 3
<211> LENGTH: 106
<212> TYPE: PRT
<213> ORGANISM: Artificial sequence
<220> FEATURE:
<223> OTHER INFORMATION: FHV B2 C-9ASM

<400> SEQUENCE: 3

Met Pro Ser Lys Leu Ala Leu Ile Gln Glu Leu Pro Asp Arg Ile Gln
1               5                   10                  15

Thr Ala Val Glu Ala Ala Met Gly Met Ser Tyr Gln Asp Ala Pro Asn
            20                  25                  30

Asn Val Arg Arg Asp Leu Asp Asn Leu His Ala Cys Leu Asn Lys Ala

```
                35                  40                  45
Lys Leu Thr Val Ser Arg Met Val Thr Ser Leu Leu Glu Lys Pro Ser
        50                  55                  60

Val Val Ala Tyr Leu Glu Gly Lys Ala Pro Glu Glu Ala Lys Pro Thr
65                  70                  75                  80

Leu Ala Ala Ala Leu Ala Leu Ala Leu Ser Ala Ser Leu Pro Thr
                85                  90                  95

Thr Gly Ser Ala Pro Pro Ala Ala Leu
            100                 105

<210> SEQ ID NO 4
<211> LENGTH: 106
<212> TYPE: PRT
<213> ORGANISM: Artificial sequence
<220> FEATURE:
<223> OTHER INFORMATION: FHV B2 K4A

<400> SEQUENCE: 4

Met Pro Ser Ala Leu Ala Leu Ile Gln Glu Leu Pro Asp Arg Ile Gln
1               5                   10                  15

Thr Ala Val Glu Ala Ala Met Gly Met Ser Tyr Gln Asp Ala Pro Asn
                20                  25                  30

Asn Val Arg Arg Asp Leu Asp Asn Leu His Ala Cys Leu Asn Lys Ala
            35                  40                  45

Lys Leu Thr Val Ser Arg Met Val Thr Ser Leu Leu Glu Lys Pro Ser
        50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Ala Lys Leu
            100                 105

<210> SEQ ID NO 5
<211> LENGTH: 106
<212> TYPE: PRT
<213> ORGANISM: Artificial sequence
<220> FEATURE:
<223> OTHER INFORMATION: FHV B2 E10A

<400> SEQUENCE: 5

Met Pro Ser Lys Leu Ala Leu Ile Gln Ala Leu Pro Asp Arg Ile Gln
1               5                   10                  15

Thr Ala Val Glu Ala Ala Met Gly Met Ser Tyr Gln Asp Ala Pro Asn
                20                  25                  30

Asn Val Arg Arg Asp Leu Asp Asn Leu His Ala Cys Leu Asn Lys Ala
            35                  40                  45

Lys Leu Thr Val Ser Arg Met Val Thr Ser Leu Leu Glu Lys Pro Ser
        50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Ala Lys Leu
            100                 105

<210> SEQ ID NO 6
<211> LENGTH: 106
```

```
<212> TYPE: PRT
<213> ORGANISM: Artificial sequence
<220> FEATURE:
<223> OTHER INFORMATION: FHV B2 D13A

<400> SEQUENCE: 6

Met Pro Ser Lys Leu Ala Leu Ile Gln Glu Leu Pro Ala Arg Ile Gln
1               5                   10                  15

Thr Ala Val Glu Ala Ala Met Gly Met Ser Tyr Gln Asp Ala Pro Asn
                20                  25                  30

Asn Val Arg Arg Asp Leu Asp Asn Leu His Ala Cys Leu Asn Lys Ala
            35                  40                  45

Lys Leu Thr Val Ser Arg Met Val Thr Ser Leu Leu Glu Lys Pro Ser
        50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Pro Ala Lys Leu
                100                 105

<210> SEQ ID NO 7
<211> LENGTH: 106
<212> TYPE: PRT
<213> ORGANISM: Artificial sequence
<220> FEATURE:
<223> OTHER INFORMATION: FHV B2 R14A

<400> SEQUENCE: 7

Met Pro Ser Lys Leu Ala Leu Ile Gln Glu Leu Pro Asp Ala Ile Gln
1               5                   10                  15

Thr Ala Val Glu Ala Ala Met Gly Met Ser Tyr Gln Asp Ala Pro Asn
                20                  25                  30

Asn Val Arg Arg Asp Leu Asp Asn Leu His Ala Cys Leu Asn Lys Ala
            35                  40                  45

Lys Leu Thr Val Ser Arg Met Val Thr Ser Leu Leu Glu Lys Pro Ser
        50                  55                  60

Val Val Ala Tyr Leu Glu Gly Lys Ala Pro Glu Glu Ala Lys Pro Thr
65                  70                  75                  80

Leu Glu Glu Arg Leu Arg Lys Leu Glu Leu Ser His Ser Leu Pro Thr
                85                  90                  95

Thr Gly Ser Asp Pro Pro Pro Ala Lys Leu
                100                 105

<210> SEQ ID NO 8
<211> LENGTH: 106
<212> TYPE: PRT
<213> ORGANISM: Artificial sequence
<220> FEATURE:
<223> OTHER INFORMATION: FHV B2 E20A

<400> SEQUENCE: 8

Met Pro Ser Lys Leu Ala Leu Ile Gln Glu Leu Pro Asp Arg Ile Gln
1               5                   10                  15

Thr Ala Val Ala Ala Ala Met Gly Met Ser Tyr Gln Asp Ala Pro Asn
                20                  25                  30

Asn Val Arg Arg Asp Leu Asp Asn Leu His Ala Cys Leu Asn Lys Ala
            35                  40                  45

Lys Leu Thr Val Ser Arg Met Val Thr Ser Leu Leu Glu Lys Pro Ser
```

```
                    50                  55                  60
Val Val Ala Tyr Leu Glu Gly Lys Ala Pro Glu Ala Lys Pro Thr
 65                  70                  75                  80

Leu Glu Glu Arg Leu Arg Lys Leu Glu Leu Ser His Ser Leu Pro Thr
                     85                  90                  95

Thr Gly Ser Asp Pro Pro Pro Ala Lys Leu
                100                 105

<210> SEQ ID NO 9
<211> LENGTH: 106
<212> TYPE: PRT
<213> ORGANISM: Artificial sequence
<220> FEATURE:
<223> OTHER INFORMATION: FHV B2 D29A

<400> SEQUENCE: 9

Met Pro Ser Lys Leu Ala Leu Ile Gln Glu Leu Pro Asp Arg Ile Gln
  1               5                  10                  15

Thr Ala Val Glu Ala Ala Met Gly Met Ser Tyr Gln Ala Ala Pro Asn
                 20                  25                  30

Asn Val Arg Arg Asp Leu Asp Asn Leu His Ala Cys Leu Asn Lys Ala
             35                  40                  45

Lys Leu Thr Val Ser Arg Met Val Thr Ser Leu Leu Glu Lys Pro Ser
 50                  55                  60

Val Val Ala Tyr Leu Glu Gly Lys Ala Pro Glu Ala Lys Pro Thr
 65                  70                  75                  80

Leu Glu Glu Arg Leu Arg Lys Leu Glu Leu Ser His Ser Leu Pro Thr
                     85                  90                  95

Thr Gly Ser Asp Pro Pro Pro Ala Lys Leu
                100                 105

<210> SEQ ID NO 10
<211> LENGTH: 16
<212> TYPE: PRT
<213> ORGANISM: Artificial sequence
<220> FEATURE:
<223> OTHER INFORMATION: FHV B2 N-terminal 16 amino acids

<400> SEQUENCE: 10

Met Pro Ser Lys Leu Ala Leu Ile Gln Glu Leu Pro Asp Arg Ile Gln
  1               5                  10                  15

<210> SEQ ID NO 11
<211> LENGTH: 26
<212> TYPE: PRT
<213> ORGANISM: Artificial sequence
<220> FEATURE:
<223> OTHER INFORMATION: FHV B2 C-terminal 26 amino acids

<400> SEQUENCE: 11

Leu Glu Glu Arg Leu Arg Lys Leu Glu Leu Ser His Ser Leu Pro Thr
  1               5                  10                  15

Thr Gly Ser Asp Pro Pro Pro Ala Lys Leu
                 20                  25

<210> SEQ ID NO 12
<211> LENGTH: 16
<212> TYPE: PRT
<213> ORGANISM: Artificial Sequence
<220> FEATURE:
<223> OTHER INFORMATION: FHV B2 N-4ASM N-terminal 16 amino acids
```

```
<400> SEQUENCE: 12

Met Pro Ser Ala Leu Ala Leu Ile Gln Ala Leu Pro Ala Ala Ile Gln
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: FHV B2 C-9ASM C-terminal 26 amino acids

<400> SEQUENCE: 13

Leu Ala Ala Ala Leu Ala Ala Leu Ala Leu Ser Ala Ser Leu Pro Thr
1               5                   10                  15

Thr Gly Ser Ala Pro Pro Pro Ala Ala Leu
            20                  25

<210> SEQ ID NO 14
<211> LENGTH: 30
<212> TYPE: PRT
<213> ORGANISM: Artificial sequence
<220> FEATURE:
<223> OTHER INFORMATION: FHV B2 N-terminal 30 amino acids

<400> SEQUENCE: 14

Met Pro Ser Lys Leu Ala Leu Ile Gln Glu Leu Pro Asp Arg Ile Gln
1               5                   10                  15

Thr Ala Val Glu Ala Ala Met Gly Met Ser Tyr Gln Asp Ala
            20                  25                  30

<210> SEQ ID NO 15
<211> LENGTH: 30
<212> TYPE: PRT
<213> ORGANISM: Artificial sequence
<220> FEATURE:
<223> OTHER INFORMATION: FHV B2 K4A N-terminal 30 amino acids

<400> SEQUENCE: 15

Met Pro Ser Ala Leu Ala Leu Ile Gln Glu Leu Pro Asp Arg Ile Gln
1               5                   10                  15

Thr Ala Val Glu Ala Ala Met Gly Met Ser Tyr Gln Asp Ala
            20                  25                  30

<210> SEQ ID NO 16
<211> LENGTH: 30
<212> TYPE: PRT
<213> ORGANISM: Artificial sequence
<220> FEATURE:
<223> OTHER INFORMATION: FHV B2 E10A N-terminal 30 amino acids

<400> SEQUENCE: 16

Met Pro Ser Lys Leu Ala Leu Ile Gln Ala Leu Pro Asp Arg Ile Gln
1               5                   10                  15

Thr Ala Val Glu Ala Ala Met Gly Met Ser Tyr Gln Asp Ala
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: FHV B2 D13A N-terminal 30 amino acids

<400> SEQUENCE: 17
```

```
Met Pro Ser Lys Leu Ala Leu Ile Gln Glu Leu Pro Ala Arg Ile Gln
1               5                   10                  15

Thr Ala Val Glu Ala Ala Met Gly Met Ser Tyr Gln Asp Ala
                20                  25                  30

<210> SEQ ID NO 18
<211> LENGTH: 30
<212> TYPE: PRT
<213> ORGANISM: Artificial sequence
<220> FEATURE:
<223> OTHER INFORMATION: FHAV B2 R14A N-terminal 30 amino acids

<400> SEQUENCE: 18

Met Pro Ser Lys Leu Ala Leu Ile Gln Glu Leu Pro Asp Ala Ile Gln
1               5                   10                  15

Thr Ala Val Glu Ala Ala Met Gly Met Ser Tyr Gln Asp Ala
                20                  25                  30

<210> SEQ ID NO 19
<211> LENGTH: 30
<212> TYPE: PRT
<213> ORGANISM: Artificial sequence
<220> FEATURE:
<223> OTHER INFORMATION: FHV B2 E20A N-terminal 30 amino acids

<400> SEQUENCE: 19

Met Pro Ser Lys Leu Ala Leu Ile Gln Glu Leu Pro Asp Arg Ile Gln
1               5                   10                  15

Thr Ala Val Ala Ala Ala Met Gly Met Ser Tyr Gln Asp Ala
                20                  25                  30

<210> SEQ ID NO 20
<211> LENGTH: 30
<212> TYPE: PRT
<213> ORGANISM: Artificial sequence
<220> FEATURE:
<223> OTHER INFORMATION: FHV B2 D29A N-terminal 30 amino acids

<400> SEQUENCE: 20

Met Pro Ser Lys Leu Ala Leu Ile Gln Glu Leu Pro Asp Arg Ile Gln
1               5                   10                  15

Thr Ala Val Glu Ala Ala Met Gly Met Ser Tyr Gln Ala Ala
                20                  25                  30
```

METHODS AND MOLECULES FOR SUPPRESSION OF RNA SILENCING

The present application claims the benefit of U.S. Provisional Patent Application Ser. No. 61/812,914, filed on Apr. 17, 2013 and hereby incorporated by reference in its entirety.

This invention was made in part with United States Government support under Grant No. 1R21AI82301, awarded by the National Institutes of Health. The U.S. Government has certain rights in this invention

FIELD OF THE INVENTIONS

Certain embodiments of the invention relate to mutant forms of flock house virus B2 protein characterized by having enhanced suppressor of RNA silencing activity as compared to wild type flock house virus B2 protein. Certain embodiments of the invention relate to nucleic acid sequences and vectors that encode and/or direct expression of such mutant forms of flock house virus B2 protein in eukaryotic cells. Certain embodiments of the invention relate to methods of using such mutant forms of flock house virus B2 protein and/or nucleic acid sequences and vectors that encode and/or direct expression thereof in eukaryotic cells to increase a replication rate of a plant or animal virus in a plant or animal cell.

BACKGROUND OF THE INVENTIONS

RNA silencing is a defense mechanism of eukaryotic cells that recognizes and destroys invasive nucleic acids such as viruses, transposons, and transgenes. (Ding, 2010; Ding and Voinnet, 2007; Ruiz-Ferrer and Voinnet, 2009.) Intracellular initiation of RNA silencing can be triggered by double-stranded RNA (dsRNA), which is processed by Dicer RNase into small interfering RNAs (siRNAs) of ~21 nucleotides (nt). siRNAs are then incorporated into RNA-induced silencing complexes (RISC) capable of guiding cycles of sequence-specific RNA degradation. Replication of RNA viral genomes often involves dsRNA intermediates that are susceptible degradation by the RNA silencing mechanism. Some RNA viral genomes encode protein suppressors of RNA silencing. (Ding, 2010; Ruiz-Ferrer and Voinnet, 2009.)

More than forty suppressor of RNA silencing proteins have been identified from plant and animal viruses. (Ding, 2010; Li and Ding, 2006; Ruiz-Ferrer and Voinnet, 2009.) These suppressor proteins can be categorized according to three, currently-identified mechanisms as follows: (i) suppression of siRNA production (e.g. HC-Pro of Potyviruses) (Llave et al., 2000); (ii) sequestration of siRNAs (e.g. p19 of Tombusviruses) (Lakatos et al., 2004; Vargason et al., 2003); and (iii) Inhibition of systemic silencing (e.g. p25 of Potato virus X) (Voinnet et al., 2000). A major function of the viral RNA silencing suppressors is to act as dsRNA-binding proteins (Li and Ding, 2006; Ruiz-Ferrer and Voinnet, 2009).

Tombusvirus p19 is a suppressor of RNA silencing that binds to 21 nt duplex siRNAs with high affinity and also binds 22 nt dsRNAs, but with lower affinity. p19 has been categorized as suppressing RNA silencing by sequestering 21 nt duplex siRNAs and prevent their incorporation into the RISC. (Lakatos et al., 2004; Vargason et al., 2003.)

SUMMARY OF THE INVENTIONS

Certain embodiments of the invention provide isolated recombinant expression vectors that comprise a promoter operably linked to a nucleic acid molecule encoding a mutant flock house virus (FHV) B2 protein that possesses: (i) a reduced ability to form a homodimer as compared to a wild type FHV B2 protein, (ii) an enhanced ability to act as a suppressor of RNA silencing as compared to a wild type FHV B2 protein, and (iii) an amino acid sequence that shares at least about 85% identity, at least about 90% identity, at least about 95% identity, or at least about 99% identity with the amino acid sequence set forth in SEQ ID NO 1. In such embodiments, the expression vector is configured to express, in at least one of a plant cell and an animal cell, the mutant FHV B2 protein encoded by the nucleic acid sequence. Also in such embodiments, the mutant FHV B2 protein comprises an alanine residue at position 4 of SEQ ID NO 1, an alanine residue at position 20 of SEQ ID NO 1, an alanine residue at position 29 of SEQ ID NO 1, or a combination thereof. In some embodiments the mutant FHV B2 protein possesses the amino acid sequence set forth in SEQ ID NO 1, SEQ ID NO 4, SEQ ID NO 8, or SEQ ID NO 9.

Certain embodiments of the invention provide isolated recombinant expression vectors that comprise a promoter operably linked to a nucleic acid molecule encoding a mutant FHV B2 protein that possesses: (i) a reduced ability to form a homodimer as compared to a wild type FHV B2 protein, (ii) an enhanced ability to act as a suppressor of RNA silencing as compared to a wild type FHV B2 protein, and (iii) an amino acid sequence that shares at least about 85% identity, at least about 90% identity, at least about 95% identity, at least about 99% identity, or 100% identity with the amino acid sequence set forth in SEQ ID NO 2. In such embodiments, the expression vector is configured to express, in at least one of a plant cell and an animal cell, the mutant FHV B2 protein encoded by the nucleic acid sequence.

Certain embodiments of the invention provide methods, of increasing a replication rate of a virus in a plant cell or an animal cell, that involve contacting a plant cell that comprises a plant virus or an animal cell that comprises an animal virus with an amount of a recombinant expression vector of according to the invention that is effective to increase a replication rate of the plant or animal virus in the plant or animal cell. In such embodiments, replication of the virus involves a dsRNA form of a genome or subgenomic fragment of the virus.

BRIEF DESCRIPTION OF THE DRAWINGS

FIG. 1A illustrates that the nucleotide (nt) sequence for the B2 open reading frame was cloned downstream of either a nt sequence that codes for an N-terminal region (amino acids 1 to 156; nYFP) region of YFP or a nt sequence that codes for a C-terminal region (amino acids 157 to 239; cYFP) of YFP in PZPn-nYFP and PZPn-cYFP, which are configured to express the fusion proteins nYFP-B2 and cYFP-B2, respectively. FIG. 1B illustrates that the B2 open reading frame was cloned upstream of either a nt sequence that codes for a N-terminal region (amino acids 1 to 156; nYFP) of YFP or a nt sequence that codes for a C-terminal region (amino acids 157 to 239; cYFP) of YFP, in PZPn-nYFP and PZPn-cYFP, which are configured to express the fusion proteins B2-nYFP and B2-cYFP, respectively.

FIG. 4A shows the structure of wild type (wt) B2 protein and truncated versions of B2 protein having 17 amino acids deleted from either the N terminus (B2Δ1-17) or C terminus (B2Δ90-106) and the amino acid sequence of the deleted region. FIG. 4A also shows the sequence of mutant versions of B2 protein B2 N-4ASM and B2 C-9ASM. In B2 N-4ASM alanine amino acids were substituted into the position of the four charged amino acids at positions 4, 10, 13, and 14 of the B2 amino acid sequence. In B2 C-9ASM alanine amino acids were substituted into the positions of the nine charged amino acids at positions 82, 83, 84, 86, 87, 89, 92, 100, and 105 of the B2 amino acid sequence.

FIG. 4B illustrates the sequence of the 30 amino acids at the N-terminus of wt B2 protein and mutants B2 K4A, B2 E10A, B2 D13A, B2 R14A, B2 E20A, B2 D29A.

DETAILED DESCRIPTION OF THE INVENTIONS

Figure 1A:
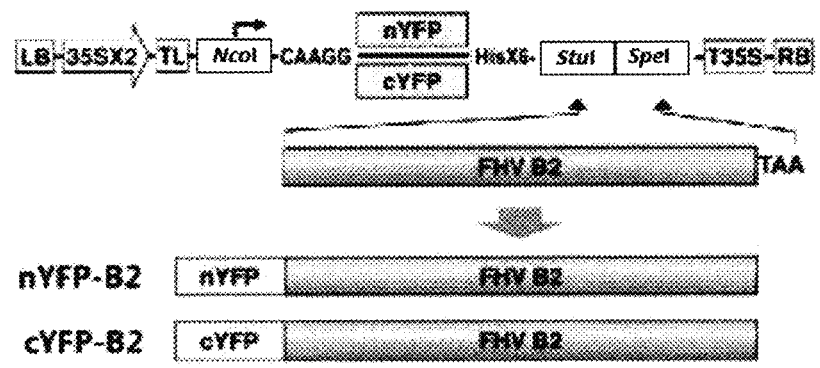
FIGS. 1A and 1B illustrate the structures of clones, and the fusion proteins they encode, used in B2 bimolecular fluorescence complementation assays performed with a yellow fluorescent protein (YFP).

Flock house virus (FHV) comprises a bipartite RNA genome: RNA1 (F1; 3.1 kb) encodes a viral RNA dependent RNA polymerase and RNA2 (F2; 1.4 kb) encodes a viral coat protein precursor (Schneemann et al., 1998). The 3' end of F1 encodes a subgenomic RNA3 (sgF3; 0.4 kb), which translates protein B2, a 12-kDa suppressor of RNA silencing that is indispensable for virus replication (Li et al., 2002; Lu et al., 2005). Some studies have reported that B2 binds with high affinity to both duplex siRNA and longer dsRNA and that B2 can protect dsRNA from Dicer cleavage in vitro. (Chao et al., 2005; Lu et al., 2005.) Other studies have reported that FHV B2 interacts with the Piwi/Argonaute/Zwille (PAZ) domain of Dicer proteins through its C-terminus and that this interaction is essential to suppress RNA silencing (Qi et al., 2012; Singh et al., 2010; Singh et al., 2009).

Certain embodiments of the invention involve recombinant expression vectors. In some embodiments, such recombinant expression vectors may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages, or viruses, to name but a few.

In some embodiments, recombinant expression vectors may include plant and/or animal expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, without limitation, genes encoding ç3-glucuronidase, ç3-galactosidase, luciferase, fluorescent proteins, such as green fluorescent protein, red fluorescent protein, and yellow fluorescent protein.

In embodiments of the present invention which utilize the *Agrobacterium* system for transforming plants, recombinant expression vectors additionally comprise at least the right T-DNA border sequence flanking the DNA sequences to be transformed into plant cells. In preferred embodiments, the sequence to be transferred is flanked by the right and left T-DNA border sequences. The design and construction of such T-DNA based transformation vectors are well known to those skilled in the art.

To use the sequences of the present invention or a combination of them or parts and/or mutants and/or fusions and/or variants of them, recombinant expression vectors can be prepared that comprise the polynucleotide sequences of the invention inserted into a vector, and which are suitable for transformation of plant and/or animal cells. The construct can be made using standard recombinant DNA techniques (Sambrook et al. 1989, the entire content of which is hereby incorporated by reference) and can be introduced to the species of interest by, e.g., in the case of plant species, *Agrobacterium*-mediated transformation or by other means of transformation including, without limitation, electroporation, heat or cold shock of cells made transformation competent by chemical treatment, and particle bombardment, such as gold particle bearing recombinant expression vector fired from a gene gun.

The vector backbone can be any of those typical in the art such as plasmids, viruses, artificial chromosomes, BACs, YACs and PACs.

Typically, a recombinant expression vector comprises a nucleic acid sequence of the present invention with any desired transcriptional and/or translational regulatory sequences, such as promoters, UTRs, and 3' end termination sequences. Vectors can also include origins of replication, scaffold attachment regions (SARs), markers, etc. The vector may also comprise a marker gene that confers a selectable phenotype on plant cells. The marker typically encodes biocide resistance, particularly antibiotic resistance, such as resistance to kanamycin, G418, bleomycin, hygromycin, or herbicide resistance, such as resistance to chlorosulfuron or phosphinotricin.

A promoter fragment can be used that directs transcription of a nucleic acid sequence of the invention in all tissues of a plant and/or animal, referred to as a constitutive promoter. Alternatively, a promoter can be used that directs transcription of a nucleic acid sequence of the invention in a specific tissue (tissue-specific promoters) or is otherwise under more precise environmental control (inducible promoters). A polyadenylation region at the 3'-end of the coding region is can included in a recombinant expression vector. The polyadenylation region can be derived from a natural gene or from various other plant or genes.

Certain embodiments of the invention, and certain aspects, parts, and/or features of embodiments of the invention, are illustrated and described in the following Figures and Examples. It will be understood that the scope of the invention extends beyond the embodiments specifically illustrated and described the Figures and Examples, to other alternative embodiments, obvious modifications, and equivalents thereof

EXAMPLE 1

Figure 1B:
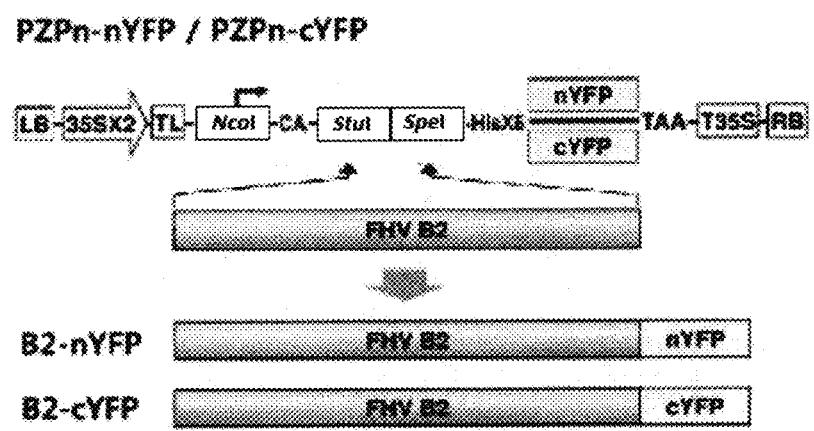

Bimolecular Fluorescence Complementation (BiFC) Assay. A BiFC assay was established based on formation of a functional fluorescent complex comprised of two subfragments of a yellow fluorescent protein (YFP). Formation of the functional florescent complex occurred via physical binding interactions between target or test proteins fused to each YFP subfragment bringing the YFP subfragments into a proximity that supports YFP fluorescence. The B2 open reading frame (ORF) was fused upstream or downstream of either the N-terminal region (amino acids 1 to 156; nYFP) or C-terminal region (amino acids 157 to 239; cYFP) of YFP (FIGS. 1A and 1B). Each pairwise combination of the nYFP or cYFP fusion protein was co-expressed by agroinfiltration in N. benthamiana leaves and YFP signals were assayed for in the epidermal cells at 3 days post infiltration (dpi) by confocal microscopy. Since successful reconstruction or formation of a functional YFP complex from YFP subfragments fused to target or test proteins depends on a variety of factors that are difficult to predict, such as structures and flexibilities of the nYFP or cYFP fusion proteins, all possible combinations of fusion proteins, which contain nYFP or cYFP at the N or C terminus, were tested for BiFC. To validate specificity of the BiFC assay, possible combinations of negative controls that did not induce any detectable fluorescence signals were tested.

Figure 2:
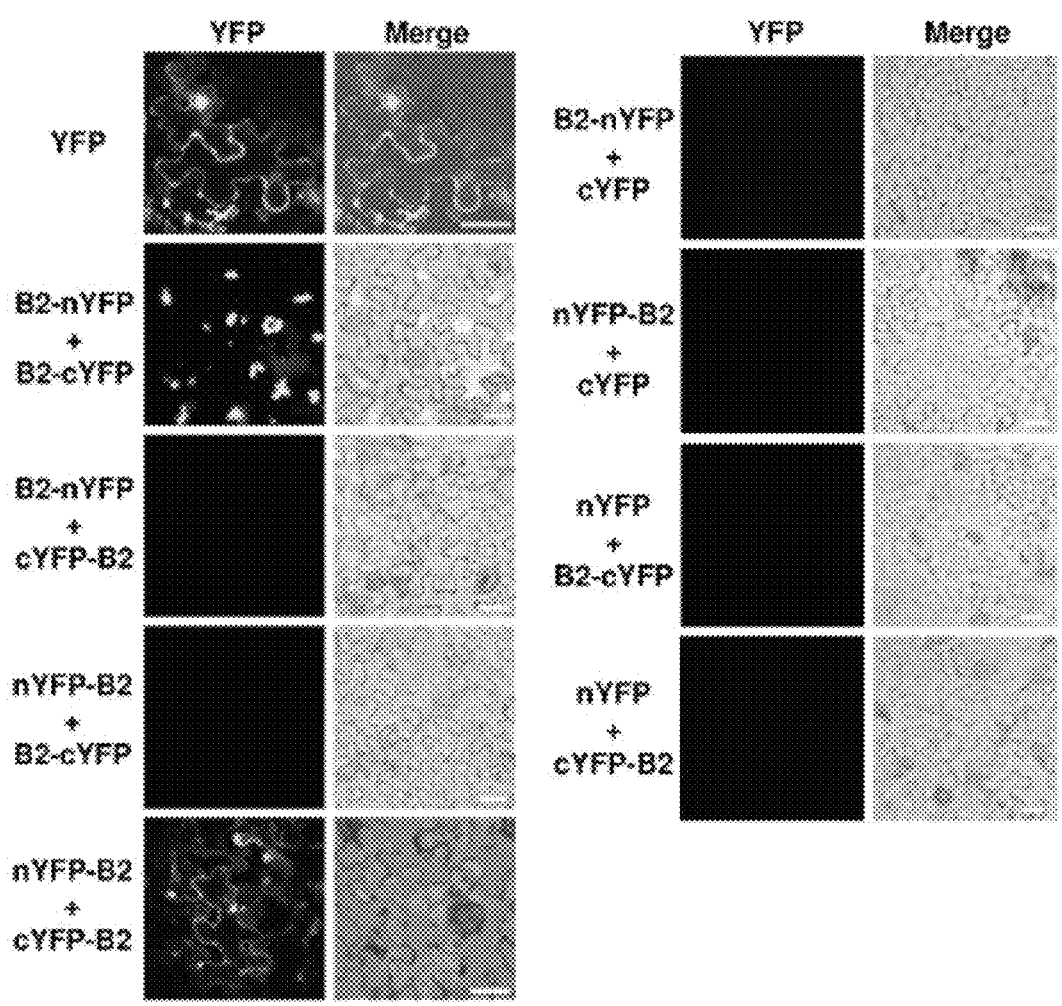
FIG. 2 shows fluorescent microscopy images and merged fluorescent-light microscopy images of a control YFP and of bimolecular fluorescence complementation assays performed in *Nicotiana benthamiana* leaves with pairwise combinations of the PZPn-nYFP, PZPn-cYFP, PZPn-nYFP, and PZPn-cYFP clones illustrated in FIGS. 1A and 1B, from which the fusion proteins nYFP-B2, cYFP-B2, B2-nYFP, and B2-cYFP are expressed, respectively

B2 dimerization was BiFC assayed. Four possible combinations of B2 fusion proteins were tested. Strong fluorescence signals were observed in the epidermal cells when a pair of either B2-nYFP+B2-cYFP or nYFP-B2+cYFP-B2 was expressed in N. benthamiana leaves (FIG. 2), indicating B2 self-interaction. YFP signals reconstructed by these two pairs showed distinguishable subcellular distribution patterns: fluorescence resulting from co-expression of B2-nYFP and B2-cYFP showed a punctate distribution while fluorescence resulting from co-expression of nYFP-B2 and cYFP-B2 was scattered throughout the cytoplasm, reminiscent of free YFP.

The subcellular localization patterns of B2 proteins N or C terminally tagged with a fluorescent protein were compared. A red fluorescent protein (RFP) and an YFP were respectively tagged to the B2 C-terminus (B2-RFP) and N-terminus (YFP-B2) and ectopically expressed in N. benthamiana leaves by agroinfiltration. The tagged B2 proteins showed different subcellular distribution profiles. YFP-B2 was distributed throughout the cytoplasm similar to free YFP; whereas B2-RFP accumulated in punctate bodies. (Data not shown.) These observations indicated that the different subcellular distribution patterns observed in B2 self-interaction are due to the tagging of additional peptides at the N or C terminus of B2.

Figure 3:
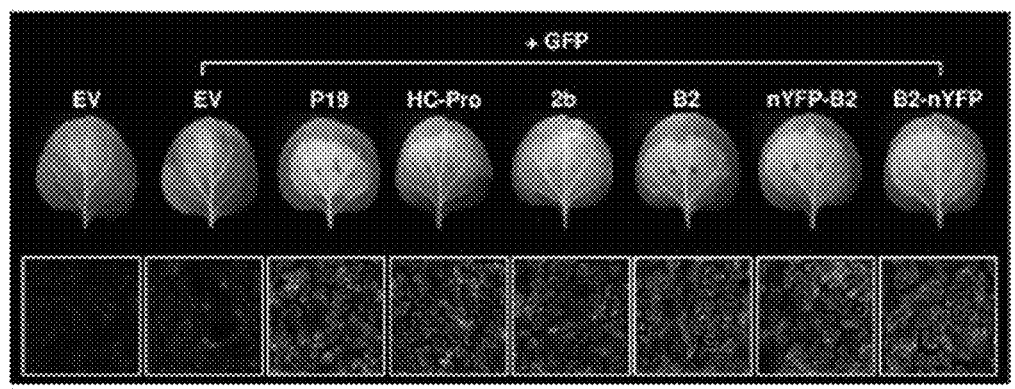
FIG. 3 shows fluorescent microscopy images of a transgene-based RNA silencing suppression assay performed in leaves of a *N. benthamiana* transgenic line expressing green fluorescent protein (GFP) with known RNA silencing suppressors P19, HC-Pro, 2b, and B2 and also with nYFP-B2 and B2-YFP proteins illustrated in FIGS. 1A and 1B.

To determine whether the N or C terminally tagged B2 proteins had suppressor of RNA silencing activity, a green fluorescent protein (GFP) transgene-based silencing suppression assay was performed. (Li et al., 2002; Lu et al., 2004; Voinnet et al., 2000, the entire content of which is hereby incorporated by reference.) The agrotransformant carrying the 35S-GFP binary vector was co-infiltrated with an agrotransformant expressing either nYFP-B2 or B2-nYFP into leaves of a N. benthamiana transgenic line expressing GFP (line 16c). A set of well characterized viral silencing suppressors such as P19 of Tomato bushy stunt virus (TBSV), HC-Pro of Tobacco etch virus (TEV), 2b of Tomato aspermy virus (TAV) and wt B2 of FHV were infiltrated into 16c plants as positive controls. At 3 dpi, GFP expression was monitored using UV light and confocal microscopy. An onset of silencing was observed in leaves infiltrated with the 35S-GFP binary vector, leading to a reduction of GFP expression, but not in plants infiltrated with positive controls (FIG. 3). Subsequently, nYFP-B2 was used in experiments designed to determine the significance of B2 dimerization as a suppressor of silencing.

EXAMPLE 2

Figure 5A:
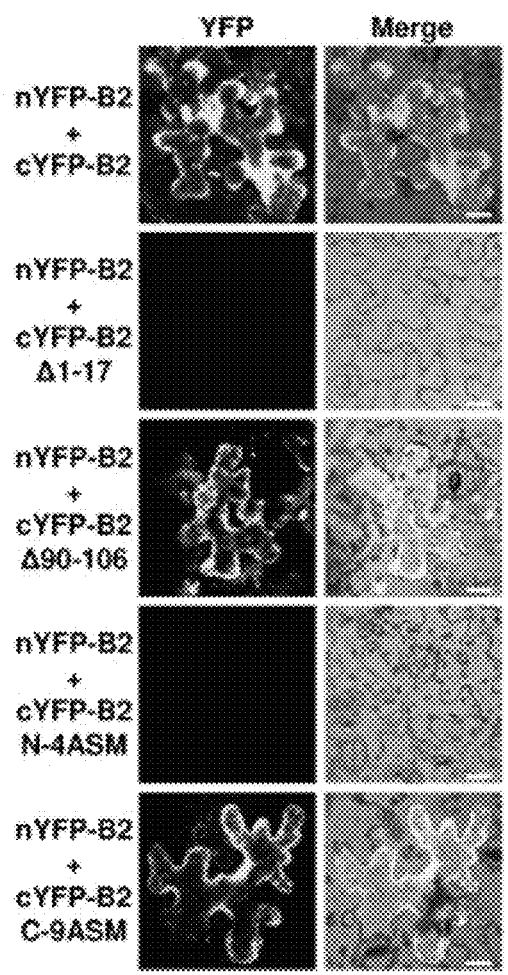
FIG. 5A shows fluorescent microscopy images and merged fluorescent-light microscopy images of bimolecular fluorescence complementation assays performed in *N. benthamiana* leaves with nYFP-B2 and a control (cYFP-B2) or cYFP fused to the truncated and alanine scanning mutant B2 proteins illustrated in FIG. 4A.

Charged Amino Acids in B2 N-Terminal Region. To determine whether charged amino acids in the N-terminal region of B2 are involved in dimerization, alanine substitutions were introduced into the 4 charged amino acids at positions 4, 10, 13 and 14 (FIG. 4A; B2 N-4ASM). As a control, an alanine substitution mutant carrying nine alanine substitutions at the C-terminus was also constructed (FIG. 4A; B2 C-9ASM). As shown in FIG. 5A, B2 dimerization was disrupted by mutations engineered into the N-terminal, 4 charged amino acids in positions 4, 10, 13 and 14 of B2 but not the C-terminus, suggesting that the charged amino acids at the N-terminus of FHV B2 are involved in the dimerization.

Figure 5B:
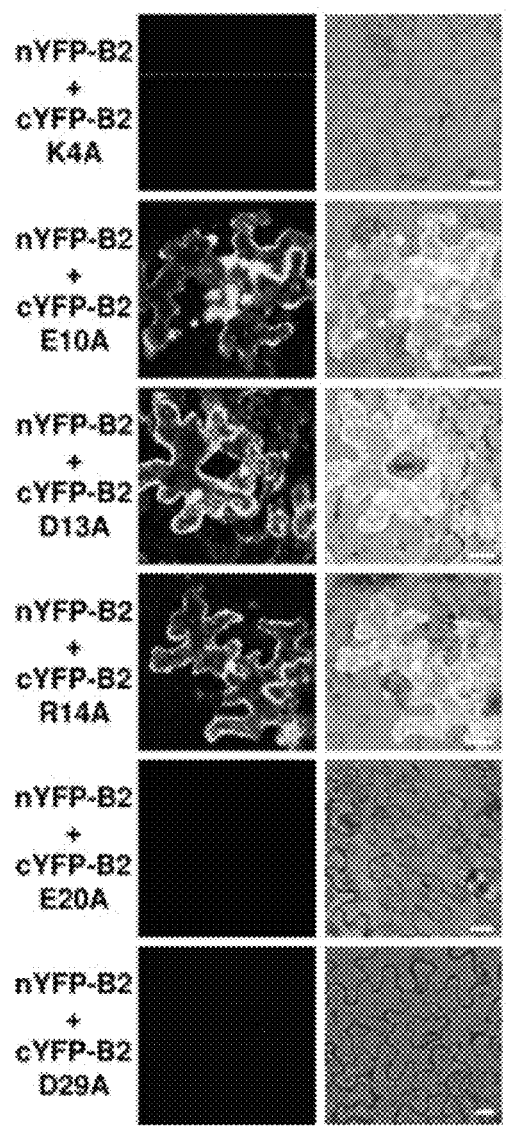
FIG. 5B shows fluorescent microscopy images and merged fluorescent-light microscopy images of bimolecular fluorescence complementation assays performed in *N. benthamiana* leaves with nYFP-B2 and cYFP fused to the single amino acid mutant B2 proteins illustrated FIG. 4B.

To further identify charged amino acid(s) of the N-terminus in B2 necessary and/or sufficient for B2 homodimerization, each charged amino acid of helix a1 at positions 4, 10, 13, 14, 20 and 29 was substituted with alanine residues (FIG. 4B). Each alanine substitution mutant was fused downstream of cYFP and subjected to BiFC assay to evaluate the effect of the engineered mutation on B2 dimerization. As shown in FIG. 5B, each mutant carrying an alanine substitution at position 4, 20, or 29 (B2 K4A, B2 E20A and B2 D29A, respectively) was defective in dimerization, suggesting that the charged residues at positions 4, 20, and 29 are important for B2 dimerization.

The charged residues were found capable of potentially forming salt bridges between two B2 monomers at their N-terminal domains: four possible salt bridges between K4 and D29' (distance 4.24 Å), R14 and E20' (distance 6.62 Å), E20 and R14' (distance 4.92 Å), and D29 and K4' (distance 4.13 Å) (Data not shown).

Figure 6A:
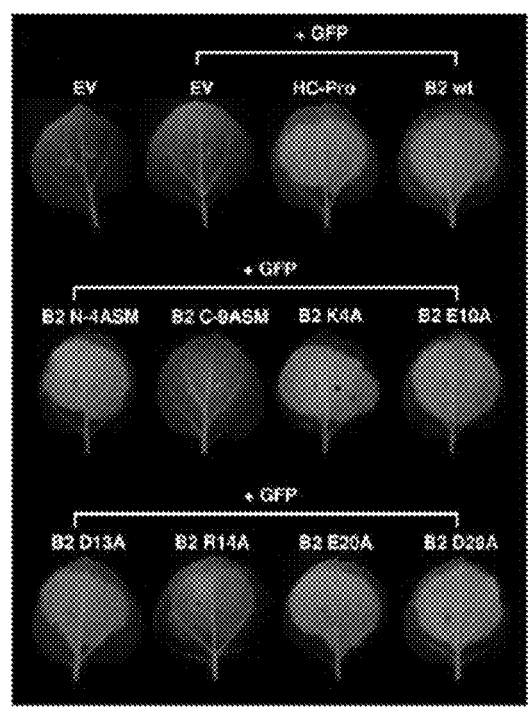
FIG. 6A shows fluorescent images of RNA silencing suppressor activity assays performed in leaves of 16c transgenic lines of *N. benthamiana* infiltrated with EV; HC-Pro; and the B2 wt, B2 N-4ASM and B2 C-9ASM mutant proteins illustrated in FIG. 4A and the B2 K4A, B2 E10A, B2 D13A, B2 R14A, B2 E20A, and B2 D29A mutant proteins illustrated in FIG. 4B.
Figure 6B:
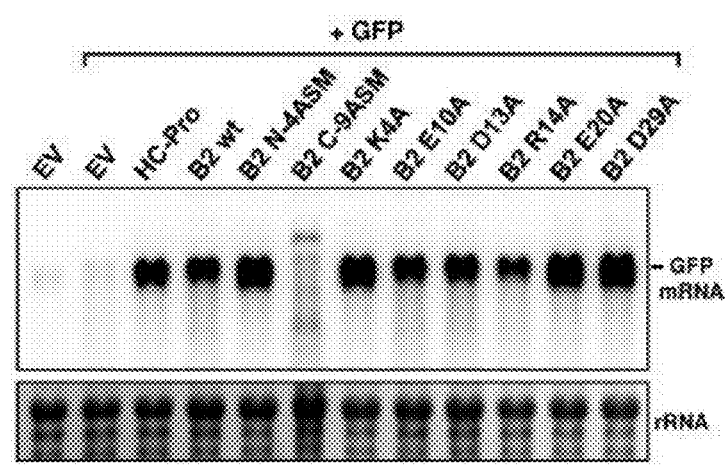
FIG. 6B shows an image of a Northern blot performed with GFP test and rRNA control probes and RNA isolated from the leaves of the 16c transgenic lines of *N. benthamiana* infiltrated with EV; HC-Pro; and the B2 wt, B2 N-4ASM and B2 C-9ASM mutant proteins illustrated in FIG. 4A and the B2 K4A, B2 E10A, B2 D13A, B2 R14A, B2 E20A, and B2 D29A mutant proteins illustrated in FIG. 4B.
Figure 6C:
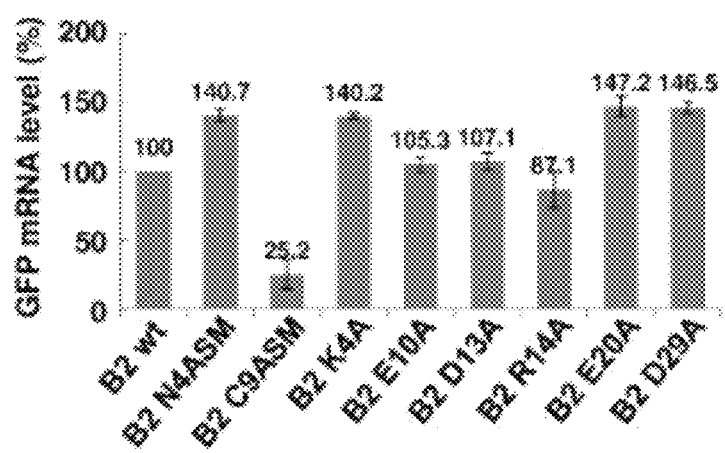
FIG. 6C is a graph of GFP mRNA levels as a percent of rRNA in the leaves of the 16c transgenic lines of *N. benthamiana* infiltrated with EV; HC-Pro; and the B2 wt, B2 N-4ASM and B2 C-9ASM mutant proteins illustrated in FIG. 4A and the B2 K4A, B2 E10A, B2 D13A, B2 R14A, B2 E20A, and B2 D29A mutant proteins illustrated in FIG. 4B.
Figure 6D:
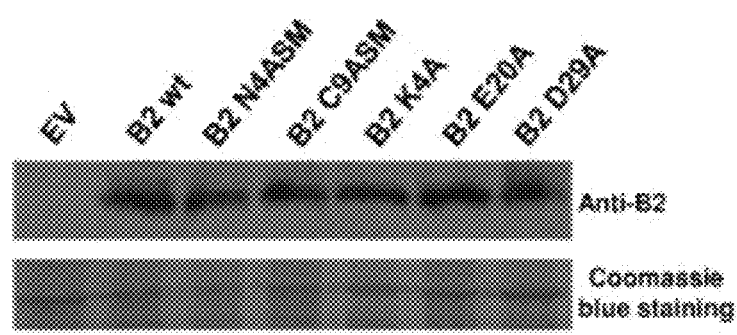
FIG. 6D shows an image of a Western blot performed with anti-B2 antibody and protein isolated from the leaves of the 16c transgenic lines of *N. benthamiana* infiltrated with the B2 wt, B2 N-4ASM and B2 C-9ASM mutant proteins illustrated in FIG. 4A and the B2 K4A, B2 E20A, and B2 D29A mutant proteins illustrated in FIG. 4B.

Non-dimerizing B2 mutants exhibit enhanced RNA silencing suppressor activity. To examine the RNA silencing suppressor activity of the alanine substitution mutants of B2, a GFP transgene silencing suppression assay as described above was performed. The agrotransformant carrying the 35S-GFP binary vector was co-infiltrated with agrotransformants that express each B2 mutant with an alanine substitution into leaves of 16c transgenic lines of N. benthamiana. 16c plants infiltrated with TEV HC-Pro and FHV wt B2 served as positive controls. At 3 dpi, suppression of RNA silencing resulting in efficient GFP expression was observed in control plants. In contrast, all B2 mutants, except mutant B2 C-9ASM, showed efficient RNA silencing suppressor activity (FIG. 6A). To quantify the transgene silencing suppression activity of each B2 mutant, accumulation of GFP mRNA was analyzed in the infiltrated leaves by Northern blot hybridization (FIG. 6B). Interestingly, all non-dimerizing mutants, B2 K4A, B2 E20A and B2 D29A, showed 40% higher RNA silencing suppressor activity than wt B2 (FIG. 6C). B2 C-9ASM failed to suppress GFP mRNA silencing; whereas B2 R14A showed slightly decreased RNA silencing suppressor activity. To determine whether the alteration of RNA silencing suppressor activity is due the stability of B2 mutant proteins, we examined the relative accumulation levels of the transiently expressed B2 wt and each mutant protein in infiltrated leaves at 3 dpi. No significant differences in the accumulation levels between wt and each mutant protein were observed (FIG. 6D), indicating that the engineered mutations did not alter the stability of the B2 protein.

EXAMPLE 3

The Effect of B2 Non-Dimerization on FHV Replication. A B2 knockout mutant of F1, referred to as F1ΔB2, which contains point mutations that abolished the synthesis of functional B2 and fails to accumulate detectable levels of viral RNAs after transfection into S2 cells has been previously described. (Li et al., 2002; Lu et al., 2005.) This defect of F1ΔB2 can be partially trans-complemented by expressing B2. (Li et al., 2002; Lu et al., 2005.)

An agrobacterium-mediated transient expression system (agroinfiltration), which facilitates the synchronized delivery and co-expression of multiple T-DNA based plasmids to the same cell, to initiate replication of FHV in N. benthamiana (Annamalai et al., 2008) was employed to test the effect of alanine substitution mutants of B2 on FHV replication by co-expressing with F1ΔB2 and F2 in N. benthamiana. FHV wt B2 and TEV HC-Pro were included as positive controls. At 5 dpi, total RNA was extracted from the infiltrated leaves and subjected to Northern blot analysis.

Figure 7:
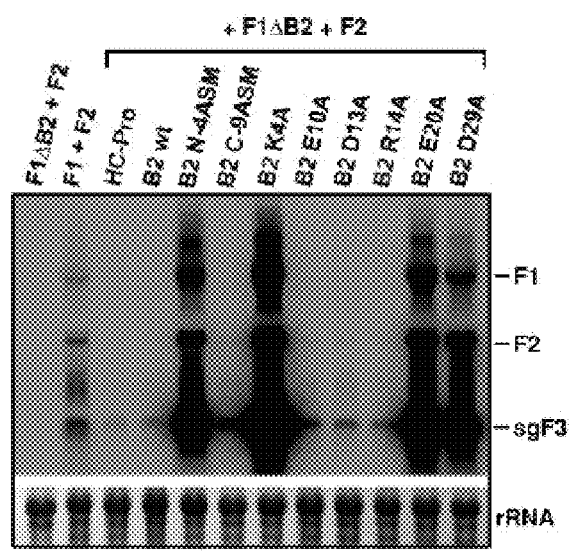
FIG. 7 shows a Northern blot performed with FHV F1 and F2 test and control rRNA probes on RNA isolated from *N. benthamiana* leaves infiltrated with F1ΔB2 and F2; wt F1 and F2; and F1ΔB2 and F2 and HC-Pro, B@ wt, B2 N-4ASM, B2 C-9ASM, B2 KA4, B2 E10A, B2 D13A, B2 R14A, B2 E20A, and B2 D29A.

FHV RNAs failed to accumulate to a detectable level in the leaves co-infiltrated with agrotransformants harboring F1ΔB2 and F2, but was detectable in leaves infiltrated with control wt F1 and F2 (FIG. 7). The accumulation levels of FHV RNA was dramatically increased when agrotransformants of F1ΔB2 and F2 were trans-complemented with the nondimerizing mutants of B2, N-4ASM, K4A, E20A, and D29A (FIG. 7).

EXAMPLE 3

FHV B2 Dimerization and PAZ Domain of RNA Silencing Machinery. The PAZ domain is found only in Dicer and Argonaute (AGO) proteins, and is highly conserved throughout the eukaryotic kingdom (Song et al., 2003). To examine whether B2 dimerization is essential for interacting with PAZ domains of Dicer proteins, we employed a yeast two-hybrid (YTH) assay. To this end, a YTH clone with a PAZ domain of Arabidopsis Dicer-like protein 1 (DCL1) served as bait while wt B2, B2 K4A, B2 D29A, and B2 C-9ASM (B2 K4A, B2 D29A are non-dimerizing B2 mutants and B2 C-9ASM carries 9 alanine substitutions at the C-terminus) (FIGS. 2C and D) acted as preys. The results of YTH assays involving interactions between PAZ domain of DCL1 and either wt B2 or its mutants are summarized in Table 1.

TABLE 1

| Plasmid combination | | Interaction | |
|---|---|---|---|
| AD | BD | Colony | β-GAL |
| pTD1-1 | pVA3-1 | +++ | Blue |
|  | pLAM5'-1 | − | White |
| B2 wt | DCL1-PAZ | ++ | Blue |
| B2 K4A | DCL1-PAZ | ++ | Blue |
| B2 D29A | DCL1-PAZ | ++ | Blue |
| B2 C-9ASM | DCL1-PAZ | − | White |

The interactions between SV40 large T antigen (84-708) (pTD1-1) and either murine p53(72-390) (pVA3-1) or human lamin C (pLAM5'-1) served as positive and (66-230) negative controls, respectively. Yeast cells co-transformed with pAD-GAL4 and pBD-GAL4 fusion derivatives were selected on SD/-LWHA agar media and their β-galactosidase activities were assayed on SD/-LW agar plates containing X-α-Gal. The number of '+' symbols indicates the comparative number of colonies formed on the SD media.

Both wt B2 and non-dimerizing mutants (B2 K4A and B2 D29A) interacted with PAZ domain of DCL1. In addition, no interaction was observed between the PAZ domain and B2 C-9ASM, indicating that the C-terminus of B2 is critical to interact with the PAZ domains. In all, these result showed that B2 dimerization is not essential for interacting with PAZ domain of DLC1.

EXAMPLE 4

Construction of Plasmids. Agroconstructs pF1 and pF2 express genomic F1 and F2 RNA, respectively. (Annamalai et al., 2008.) A sequence encompassing FHV B2 was amplified by PCR and inserted into StuI and SpeI digested plasmids PZPc-nYFP, PZPc-cYFP, PZPn-nYFP or PZPn-cYFP, as described previously (Seo et al., 2012). PCR was used to engineer deletions and amino acid substitutions into either the N- or C-terminus of B2. Each B2 mutant was inserted downstream of cYFP to express the desired fusion proteins, or inserted into PZP vector digested with StuI and SpeI to produce B2 and its mutants as non-fusion proteins. Plasmid pF1ΔB2A harboring a B2 knockout mutant of F1 was constructed by amplifying the full-length cDNA of F1 carrying the B2 knockout mutation in a PCR reaction using pFR1-3ΔB2 (Lu et al., 2005; kindly provided by Dr. Ding) as a template and an appropriate pair of primers, followed by subcloning into StuI digested pCassRz vector. To construct the Yeast Two-Hybrid (YTH) clones, B2 and its mutants were amplified by PCR and inserted into EcoRI and PstI digested pAD-GAL4-2.1 plasmid (Stratagene, USA). The PAZ domain of Arabidopsis DCL1 was amplified by PCR and inserted into SalI and PstI digested pBD-GAL4 cam plasmid (Stratagene, USA). DNA sequencing was used to verify the recombinant nature of each construct.

EXAMPLE 5

Agroinfiltration for BiFC and Confocal Microscopy. Following transformation of binary vectors into *Agrobacterium* strain GV3101, each *Agrobacterium* culture containing the desired agrotransformant (0.2 at OD600) was infiltrated into *N. benthamiana* leaves (Annamalai and Rao, 2005; Seo et al., 2009). At 3 dpi, epidermal cells of agro-infiltrated leaves were observed for emission of fluorescence using a Leica SP2 laser-scanning confocal microscope (Leica, Germany) equipped with a specific laser/filter combination to detect YFP (excitation at 514 nm) and RFP (excitation at 594 nm).

EXAMPLE 6

Analysis of the Three-Dimensional Structure of the B2-dsRNA Complex. The structural data of the B2-dsRNA complex deposited in the PDB database (PBD ID: 2AZO; Chao et al., 2005) was analysed using Jmol version 12.0.41 (Research Collaboratory for Structural Bioinformatics).

EXAMPLE 7

Transgene Silencing Suppression Assay. The agroconstruct 35S-GFP (kindly provided by Dr. Shou-Wei Ding) expressing GFP mRNA in planta was described previously (Lu et al., 2004). For coinfiltration assays, equal volumes of agrotransformants harboring 35S-GFP and either B2 or one of its mutants were mixed and infiltrated into leaves of a *N. benthamiana* transgenic line expressing GFP (line 16c). At 3 dpi, the GFP fluorescence in the infiltrated leaves was visualized by using a hand-held long wave UV-light source (Blak-Ray B-100AP, Ultraviolet Products, USA) and photographed. To analyze GFP mRNA accumulation levels, at 3 dpi, total RNA was extracted from the infiltrated area using TRIzol reagent (Invitrogen, USA) and subjected to Northern blotting using a riboprobe complementary to full-length GFP as described previously (Lu et al., 2004).

EXAMPLE 8

FHV Progeny Analysis. Total RNAs extracted from infiltrated leaves were subjected to Northern blot hybridization for FEV progeny RNA detection using riboprobes complementary to either F1 or F2, as described previously (Annamalai et al., 2008).

EXAMPLE 9

Amino Acid Sequences of Wild Type and Mutant FHV B2 Proteins. Table 2 lists the SEQ ID NOs corresponding to wild type and mutant FHV B2 proteins.

TABLE 2

| | |
|---|---|
| Wild type FHV B2 | SEQ ID NO 1 |
| FHV B2 N-4ASM | SEQ ID NO 2 |
| FHV B2 c-9ASM | SEQ ID NO 3 |
| FHV B2 KK4A | SEQ ID NO 4 |
| FHV B2 E10A | SEQ ID NO 5 |
| FHV B2 D13A | SEQ ID NO 6 |
| FHV B2 R14A | SEQ ID NO 7 |
| FHV B2 E20A | SEQ ID NO 8 |
| FHV B2D29A | SEQ ID NO 9 |

EXAMPLE 9

Yeast Two-Hybrid Assay. Yeast two hybrid assay was conducted based on the HybriZAP 2.1 Two-Hybrid System (Stratagene, USA). Competent cells of yeast strain AH109 were co-transformed with the pAD-GAL4 and pBD-GAL4 fusion derivatives by the lithium acetate method (Seo et al., 2010) and then selected on synthetic dropout (SD) agar media either lacking leucine, tryptophan, histidine and adenine (-LWHA) or lacking leucine and tryptophan (-LW). The interactions between SV40 large T antigen (84-708) (pTD1-1) and either murine p53(72-390) (pVA3-1) or human lamin C(66-230) (pLAM5'-1) served as positive and negative controls, respectively. All interactions were confirmed by βgalactosidase activity assays using the SD/-LW and SD/-LWHA agar plates containing X-α-Gal reagent (Clontech, USA).

The following publications are hereby incorporated by reference in their entirety:

Annamalai, P., Rao, A L., 2005. Replication-independent expression of genome components and capsid protein of brome mosaic virus in planta: a functional role for viral replicase in RNA packaging. Virology 338, 96-111.

Annarnalai, P. Rofail, F., Demason, D. A., Rao, A. L., 2008. Replication-coupled packaging mechanism in positive-strand RNA viruses: synchronized coexpression of functional multigenome RNA components of an animal and a plant virus in *Nicotiana benthamiana* cells by agroinfiltration. J Virol 82, 1484-1495.

Barlow, D. J., Thornton, J. M., 1983. ion-pairs in proteins. J Mol Biol 168, 667-885.

Brandt, T. A., Jacobs, B. L., 2001. Both carboxy- and amino-terminal domains of the vaccinia virus interferon resistance gene, ER, are required for pathogenesis in a mouse model. J Virol 75, 850-856.

Chao, J. A., Lee, J. H., Chapados, B. R., Debler, E. W., Schneemann, A., Williamson, J. R., 2005. Dual modes of RNA-silencing suppression by Flock House virus protein B2. Nat Struct Mol Biol 12, 952-957. Chien, C. Y., Xu, Y., Xiao, R., Aramini, J. M., Sahasrabudhe, P. V., Krug, R. M., Montelione, G. T., 2004. Biophysical characterization of the complex between double-stranded RNA and the N-terminal domain of the NS1 protein from influenza A virus: evidence for a novel RNA-binding mode. Biochemistry 43, 1950-1962

Ding, S. W., 2010. RNA-based antiviral immunity. Nat Rev Immunol 10, 6P-644

Ding, S. W., Voinnet, O., 2007. Antiviral immunity directed by small RNAs. Cell 130, 413-426.

Fenner, B. J., Goh, W., Kwang, J. 2006. Sequestration and protection of double-stranded RNA by the betanodavirus b2 protein. J Virol 80, 6822-6833.

Fenner, B. J., Goh, W., Kwang, J., 2007. Dissection of double-stranded RNA binding protein B2 from betanodavirus. J Virol 81, 5449-5459.

Kerppola, T. K., 2008. Bimolecular fluorescence complementation: visualization of molecular interactions in living cells. Methods Cell Biol 85, 431-470.

Lakatos, L., Szittya, G., Silhavy, D., Burgyan, J., 2004. Molecular mechanism of RNA silencing suppression mediated by p19 protein of tombusviruses. EMBO J 23, 876-884.

Li, F., Ding, S. W., 2006. Virus counterdefense: diverse strategies for evading the RNA-silencing immunity. Annu Rev Microbiol 60, 503-531.

Li, H., Li, W. X., Ding, S W., 2002. Induction and suppression of RNA silencing by an animal virus. Science 296, 1319-1321.

Lingel, A., Simon, B., izaurralde, E., Sattler, M., 2005. The structure of the flock house virus B2 protein, a viral suppressor of RNA interference, shows a novel mode of double-stranded RNA recognition. EMBO Rep 6, 1149-1155.

Llave, C., Kasschau, K. D., Carrington, J. C., 2000. Virus-encoded suppressor of posttranscriptional gene silencing targets a maintenance step in the silencing pathway. Proceedings of the National Academy of Sciences of the United States of America 97, 13401-13406.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc Natl Acad Sci USA 101, 15742-15747.

Lu, R., Maduro, M., Li, F., Li, H. W., Broitman-Maduro, G., Li, W. X., Ding, S. W., 2005. Animal virus replication and RNAi-mediated antiviral silencing in *Caenorhabditis elegans*. Nature 436, 1040-1043.

Mallory, A., Vaucheret H., 2010. Form; function and regulation of ARGONAUTE proteins. Plant Cell 22, 3879-3889.

Marston, F. A., 1986. The purification of eukaryotic polypeptides synthesized in *Escherichia coli*. Biochem J 240, 1-12.

Matzke, M. A., Primig, M., Trnovsky, J., Matzke, A. J., 1989. Reversible methylation and inactivation of marker genes in sequentially transformed tobacco plants. EMBO J 8, 643-649.

Miller, D. J., Schwartz, M. D., Ahlquist, P., 2001. Flock house virus RNA replicates on outer mitochondrial membranes in *Drosophila* cells. J Virol 75, 11664-11676.

Napoli, C., Lemieux, C., Jorgensen, R., 1990. Introduction of a Chimeric Chalcone Synthase Gene into *Petunia* Results in Reversible Co-Suppression of Homologous Genes in trans. Plant Cell 2, 279-289.

Qi, N., Cai, D., Qiu, Y., Xie, J., Wang, Z., Si, J., Zhang, J., Zhou, X., Hu, Y., 2011. RNA binding by a novel helical fold of b2 protein from wuhan nodavirus mediates the suppression of RNA interference and promotes b2 dimerization. J Virol 85, 9543-9554.

Qi, N., Zhang, L., Qiu, Y., Wang, Z., Si, J., Liu, Y., Xiang, X., Xie, J., Qin, C.-F., Zhou, X., Hu, a. Y., 2012. Targeting of Dicer-2 and RNA by a Viral RNA silencing Suppressor in *Drosophila* Cells J. Virol. doi:10.1128/JVI.07229-11

Ruiz-Ferrer, V., Voinnet, O., 2009. Roles of plant small RNAs in biotic stress responses. Annu Rev Plant Biol 60, 485-510.

Schneemann, A., Reddy, V., Johnson, J. E., 1998. The structure and function of nodavirus particles: a paradigm for understanding chemical biology. Adv Virus Res 50, 381-446.

Scotti, P. D., Dearing, S., Mossop, D. W., 1983. Flock House virus: a nodavirus isolated from Costelytra zealandica (White) (Coleoptera: Scarabaeidae). Arch Virol 75, 181-189.

Seo, J.-K., Kwon, S.-J., Rao, A. L. N., 2012. A Physical Interaction between Viral Replicase and Capsid protein is Required for Genome Packaging Specificity in an RNA Virus. J. Virol. doi:10.1128/JVI.07184-11.

Seo, J. K., Kang, S. H., Seo, B. Y., Jung, J. K., Kim, K. H., 2010. Mutational analysis of interaction between coat protein and helper component-proteinase of Soybean mosaic virus involved in aphid transmission. Mol Plant Pathol 11, 265-276.

Seo, J. K., Kwon, S. J., Choi, H. S., Kim, K. H., 2009. Evidence for alternate states of Cucumber mosaic virus replicase assembly in positive- and negative-strand RNA synthesis. Virology 383, 248-260.

Seo, J. K., Kwon, S. J., A L N Rao, 2012. Molecular dissection of Flock house virus protein B2 reveals that electrostatic interactions between N-terminal domains of B2 monomers are critical for dimerization. Virology 432(2), 296-305.

Singh, G., Korde, R., Malhotra, P., Mukherjee, S., Bhatnagar, R. K., 2010. Systematic deletion and site-directed mutagenesis of FHVB2 establish the role of C-terminal amino acid residues in RNAi suppression. Biochem Biophys Res Commun 398, 290-295.

Singh, G., Popli, S., Hari, Y., Malhotra, P., Mukherjee, S., Bhatnagar, R. K., 2009. Suppression of RNA silencing by Flock house virus B2 protein is mediated through its interaction with the PAZ domain of Dicer. FASEB J 23, 1845-1857.

Song, J. J., Liu, J., Tolia, N. H., Schneiderman, J., Smith, S. K., Martienssen, R. A., Hannon, G. J., Joshua-Tor, L., 2003. The crystal structure of the Argonaute2 PAZ domain reveals an RNA binding motif in RNAi effector complexes. Nat Struct Biol 10, 1026-1032.

Vargason, J. M., Szittya, G., Burgyan, J., Hall, T. M., 2003. Size selective recognition of siRNA by an RNA silencing suppressor. Cell 115, 799-811.

Vaucheret, H., Beclin, C., Fagard, M., 2001. Post-transcriptional gene silencing in plants. J Cell Sci 114, 3083-3091.

Voinnet, O., 2005. Induction and suppression of RNA silencing: insights from viral infections. Nat Rev Genet 6, 206-220.

Voinnet, O., Lederer, C., Baulcombe, D. C., 2000. A viral movement protein prevents spread of the gene silencing signal in *Nicotiana benthamiana*. Cell 103, 157-167.

Wurth, C., Guimard, N. K., Hecht, M. H., 2002. Mutations that reduce aggregation of the Alzheimer's Abeta42 peptide: an unbiased search for the sequence determinants of Abeta amyloidogenesis. J Mol Biol 319, 1279-1290.

Zamore, P. D., 2001. RNA interference: listening to the sound of silence. Nat Struct Biol 8, 746-750.

Although the disclosure has been provided in the context of certain embodiments and examples, it will be understood by those skilled in the art that the disclosure extends beyond the specifically described embodiments of polypeptide and nucleic acid sequences. Accordingly, the disclosure is exemplary and not intended to be limited by the specific disclosures of embodiments herein.

What is claimed is:

1. An isolated recombinant expression vector comprising a promoter operably linked to a nucleic acid molecule encoding a mutant flock house virus (FHV) B2 protein that possesses:
   (i) a reduced ability to form a homodimer as compared to a wild type FHV B2 protein,
   (ii) an enhanced ability to act as a suppressor of RNA silencing as compared to a wild type FHV B2 protein, and
   (iii) an amino acid sequence that shares at least about 85% identity with the amino acid sequence set forth in SEQ ID NO: 1,
wherein:
   the expression vector is configured to express, in at least one of a plant cell and an animal cell, the mutant FHV B2 protein encoded by the nucleic acid sequence, and the mutant FHV B2 protein comprises an alanine residue at position 4 of SEQ ID NO: 1, an alanine residue at position 20 of SEQ ID NO: 1, an alanine residue at position 29 of SEQ ID NO: 1, or a combination thereof.

2. The isolated recombinant expression vector of claim 1, wherein the mutant FHV B2 protein possesses an amino acid sequence that shares at least about 90% identity with the amino acid sequence set forth in SEQ ID NO: 1.

3. The isolated recombinant expression vector of claim 1, wherein the mutant FHV B2 protein possesses an amino acid sequence that shares at least about 95% identity with the amino acid sequence set forth in SEQ ID NO: 1.

4. The isolated recombinant expression vector of claim 1, wherein the mutant FHV B2 protein possesses an amino acid sequence that shares at least about 99% identity with the amino acid sequence set forth in SEQ ID NO: 1.

5. The isolated recombinant expression vector of claim 1, wherein the mutant FHV B2 protein possesses the amino acid sequence set forth in SEQ ID NO: 4.

6. The isolated recombinant expression vector of claim 1, wherein the mutant FHV B2 protein possesses the amino acid sequence set forth in SEQ ID NO: 8.

7. The isolated recombinant expression vector of claim 1, wherein the mutant FHV B2 protein possesses the amino acid sequence set forth in SEQ ID NO: 9.

8. An isolated recombinant expression vector comprising a promoter operably linked to a nucleic acid molecule encoding a mutant FHV B2 protein that possesses:
    (i) a reduced ability to form a homodimer as compared to a wild type FHV B2 protein,
    (ii) an enhanced ability to act as a suppressor of RNA silencing as compared to a wild type FHV B2 protein, and
    (iii) an amino acid sequence that shares at least about 85% identity with the amino acid sequence set forth in SEQ ID NO: 2,
wherein:
    the expression vector is configured to express, in at least one of a plant cell and an animal cell, the mutant FHV B2 protein encoded by the nucleic acid sequence, and wherein the mutant FHV B2 protein comprises an alanine residue at position 4 of SEQ ID NO:2.

9. The isolated recombinant expression vector of claim 8, wherein the mutant FHV B2 protein possesses an amino acid sequence that shares at least about 90% identity with the amino acid sequence set forth in SEQ ID NO: 2.

10. The isolated recombinant expression vector of claim 8, wherein the mutant FHV B2 protein possesses an amino acid sequence that shares at least about 95% identity with the amino acid sequence set forth in SEQ ID NO: 2.

11. The isolated recombinant expression vector of claim 8, wherein the mutant FHV B2 protein possesses an amino acid sequence that shares at least about 99% identity with the amino acid sequence set forth in SEQ ID NO: 2.

12. The isolated recombinant expression vector of claim 8, wherein the mutant FHV B2 protein possesses the amino acid sequence set forth in SEQ ID NO: 2.

13. A method, of increasing a replication rate of a virus in a plant cell, comprising: contacting a plant cell that comprises a virus with an amount of the recombinant expression vector of claim 1 effective to increase a replication rate of the virus in the plant cell, wherein the expression vector is configured to express, in the plant cell, the mutant FHV B2 protein encoded by the nucleic acid sequence, and wherein replication of the virus in the plant cell involves a dsRNA form of a genome or subgenomic fragment of the virus.

14. A method, of increasing a replication rate of a virus in an isolated animal cell, comprising: contacting an isolated animal cell that comprises a virus with an amount of the recombinant expression vector of claim 1 effective to increase a replication rate of the virus in the animal cell, wherein the expression vector is configured to express, in the animal cell, the mutant FHV B2 protein encoded by the nucleic acid sequence, and wherein replication of the virus in the animal cell involves a dsRNA form of a genome or subgenomic fragment of the virus.

15. A method, of increasing a replication rate of a virus in a plant cell, comprising: contacting a plant cell that comprises a virus with an amount of the recombinant expression vector of claim 8 effective to increase a replication rate of the virus in the plant cell, wherein the expression vector is configured to express, in the plant cell, the mutant FHV B2 protein encoded by the nucleic acid sequence, and wherein replication of the virus in the plant cell involves a dsRNA form of a genome or subgenomic fragment of the virus.

16. A method, of increasing a replication rate of a virus in an isolated animal cell, comprising: contacting an isolated animal cell that comprises a virus with an amount of the recombinant expression vector of claim 8 effective to increase the replication rate of the virus in the animal cell, wherein the expression vector is configured to express, in the animal cell, mutant FHV B2 protein encoded by the nucleic acid sequence, and wherein replication of the virus in the plant involves a dsRNA form of a genome or subgenomic fragment of the virus.

\* \* \* \* \*